US00PP08497P

United States Patent [19]

Rivoira

[11] Patent Number: Plant 8,497

[45] Date of Patent: Dec. 14, 1993

[54] KIWI PLANT NAMED K1 89

[75] Inventor: Pier G. Rivoira, Verzuolo, Italy

[73] Assignee: Agricola Kiwi S.a.s. di Lombardi Francesco & C, Quartesana, Italy

[21] Appl. No.: 811,022

[22] Filed: Dec. 20, 1991

[30] Foreign Application Priority Data

Dec. 21, 1990 [IT] Italy ..... 00230NV/90

[51] Int. Cl.[5] ..... A01H 5/00

[52] U.S. Cl. ..... Plt./33.1

[58] Field of Search ..... Plt./33.1

[56] References Cited

U.S. PATENT DOCUMENTS

P.P. 6,815 5/1989 Wilkins et al. ..... Plt. 33.1

*Primary Examiner*—James R. Feyrer

*Attorney, Agent, or Firm*—Christie, Parker & Hale

[57] ABSTRACT

A new variety of Kiwi plant of the species *Actinidia chinensis* Pl. having brownish-red fruit skin.

3 Drawing Sheets

BACKGROUND OF THE INVENTION

Kiwi plants are of the species Actinidia which are deciduous vines native to East Asia. Plants produce attractive foliage but require supports to twine upon.

Kiwi plants are typically pruned and shaped for form and fruit production in the winter. Fruit is borne on shoots from year old or older wood. For best production shoots that have fruited for three years are generally removed.

*Actinidia chinensis,* also known as Chinese gooseberry, produces long vines which can reach 30 feet if not curbed. Leaves are generally five to eight inches long, round, dark green above and velvety white underneath. New growth may have a red fuzz. The flowers are typically 1 to 1½ inches wide and open cream colored and fade to buff. Fruit is typically egg sized, roughly egg shaped, and covered with a brown fuzz. Both male and female plants are required for fruit production. One of the best female fruiting varieties is the variety 'Hayward'.

SUMMARY OF THE INVENTION

The present invention relates to a new and distinct variety of Kiwi plant, which was originated by me by selection from unnamed and unpatented seedlings of my creation grown in a controlled planting. The varietal denomination of the new variety is 'K1 89'.

Among the novel characteristics possessed by this new variety which distinguishes it from all other varieties of which I am aware are its brownish-red fruit skin, lack of long hair and a silky aspect. The new variety can be asexually reproduced through propagation by cutting and/or grafting, as well as other recognized techniques for asexual reproduction. Asexual reproduction by cutting and grafting as performed in Verzuolo (Cuneo) Italy, shows that the foregoing and other distinguishing characteristics come true to form and are established and transmitted through succeeding propagation.

As is the case for all the species of *Actinidia chinensis,* the viability of male organs is reduced with atrophied stamens and therefore is essentially self-sterile, i.e, cannot be self-pollinated. Consequently, it is necessary that male plants be present to assure a regular pollination. From tests carried out to date, the variety 'K1 89' has shown to be compatible with male plants of the varieties 'Matua' and 'Tomuri'.

BRIEF DESCRIPTION OF ILLUSTRATIONS

The accompanying illustrations show typical specimens of the flowers and fruit of the new variety depicted in color as nearly true as it is reasonably possible to make the same in a color illustration of this character. Colors may vary depending upon growing conditions under different climate, soil, and cultivation conditions and the fruit skin color may vary depending upon extent of exposure to direct sunlight.

COMPARISON TO CLOSEST VARIETY

Figure 1:
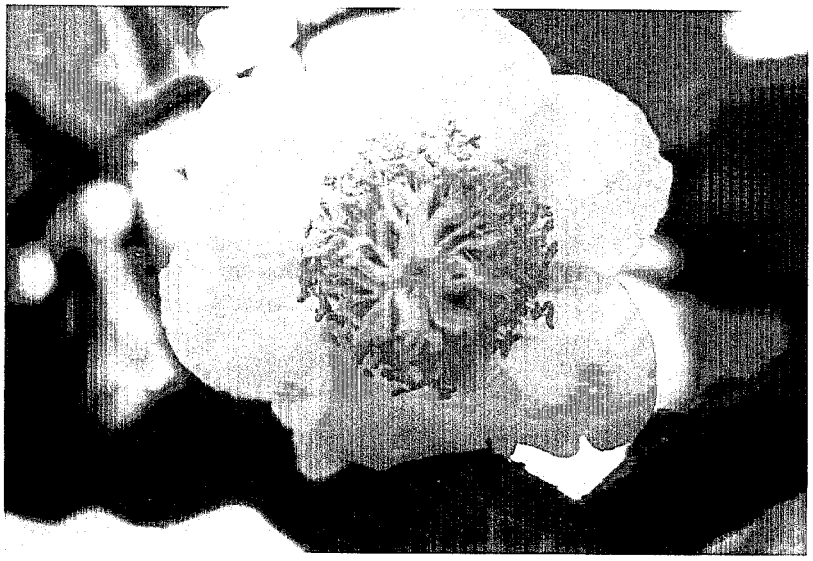
FIG. 1 is of a flower of the new variety.

The closest variety to 'K1 89' of which I am aware is the variety 'Hayward'. The new variety differs from 'Hayward' in absence of hairs on the skin of the fruit and on the branches of the plant; in flowering time — the new variety flowers about 10 days earlier than 'Hayward' and the vegetation is more restrained; in internode placement — the internodes of the fruit buds are closer together in the new variety than in the variety 'Hayward', and; in the color of the flesh of the fruit, which is light green compared to dark green in 'Hayward'. In addition, the flesh of the new variety is more aromatic than 'Hayward'.

Fruit of the new variety ripens normally 15 to 20 days before the variety 'Hayward' and the sugar content of the fruit, (determined refractometrically), is 1°-1.5° Brix higher than the sugar content of the variety 'Hayward' as determined at complete ripening.

As indicated previously, the skin of the new variety has been described as essentially hairless and the surface has a "silky" aspect. This is in contrast to the fruit of the variety 'Hayward' which has very long hairs.

The following additional information is provided to compare the new variety with 'Hayward'. These comparisons were made from a a controlled planting in the Zona Verzuolo (Cuneo), Northern Italy.

| | |
|---|---|
| **1991** | |
| Flowering date -- 10% open flowers: | |
| 'K1 89' | May 25 |
| 'Hayward' | June 4 |
| 90-100% open flowers: | |
| 'K1 89' | May 31 |
| 'Hayward' | June 12 |
| **1992** | |
| Flowering date -- 10% open flowers: | |
| 'K1 89' | May 14 |
| 'Hayward' | May 21 |
| 90-100% open flowers: | |
| 'K1 89' | May 27 |
| 'Hayward' | May 28 |

The vigor of the new variety, insofar as it is possible to deduce from internode length, branch length and general habit of growth of the plant, is somewhat less than 'Hayward'. However, the new variety 'K1 89' exhibits a higher percentage of new sprouts and buds and a greater fertility of the shoots, in terms of fruit production, than that of the variety 'Hayward'.

DETAILED DESCRIPTION OF THE NEW VARIETY

The new variety 'K1 89' is of female sex expression and requires a pollinating plant for fruit production. At the present time pollinating plants used are selected from a number of unpatented and unnamed seedlings of my creation.

Features of the new variety include early flowering and harvesting response and the physical and visual appearance of the skin of the fruit. The fruit skin of 'K1 89' tends to be smooth and presents a "silky" aspect. Plants of the new variety have smooth branches and the flesh of the fruit is light green.

Unless otherwise indicated the description of my new variety, herein includes color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

As can be seen in the accompanying illustrations,

FIG. 1 shows a flower of the new variety depicting an open bloom with six near white petals.

Figure 2:
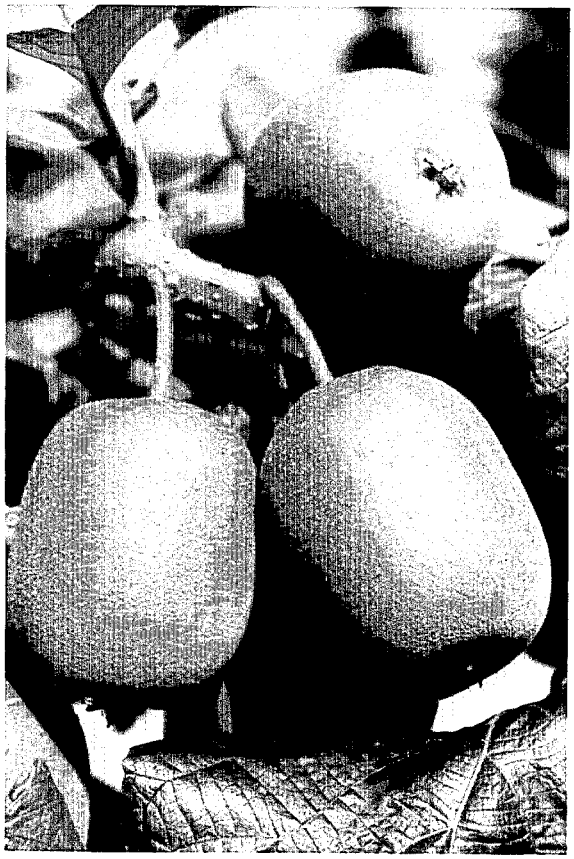
FIG. 2 shows the fruit of the new variety.

FIG. 2 shows fruit of the new variety.

Figure 3:
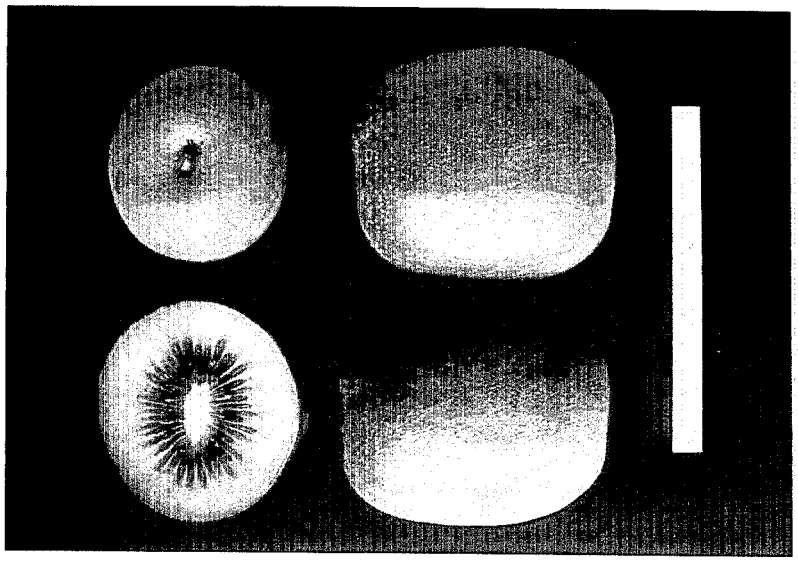
FIG. 3 shows top and lateral views of the fruit with a transverse section of same.

FIG. 3 shows top and lateral views of the fruit with a transverse section of same.

Figure 4:
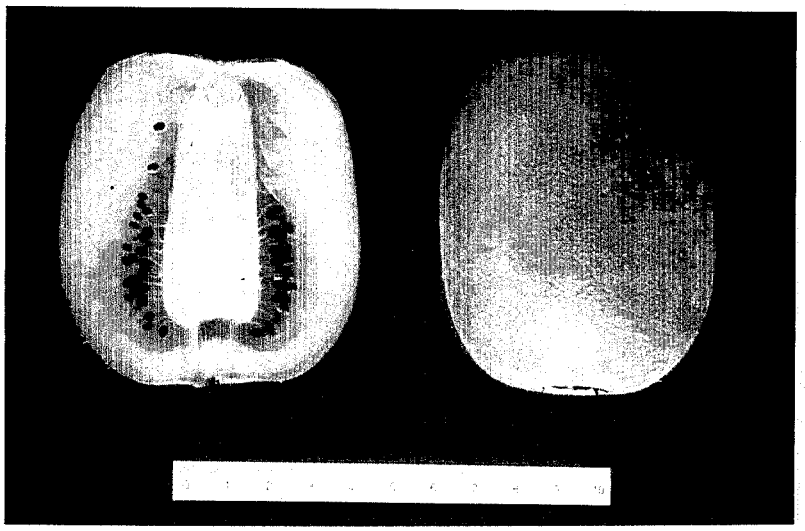
FIG. 4 shows a lateral view of the fruit and a lateral section.

FIG. 4 shows a lateral view of the fruit and a lateral section.

Figure 5:
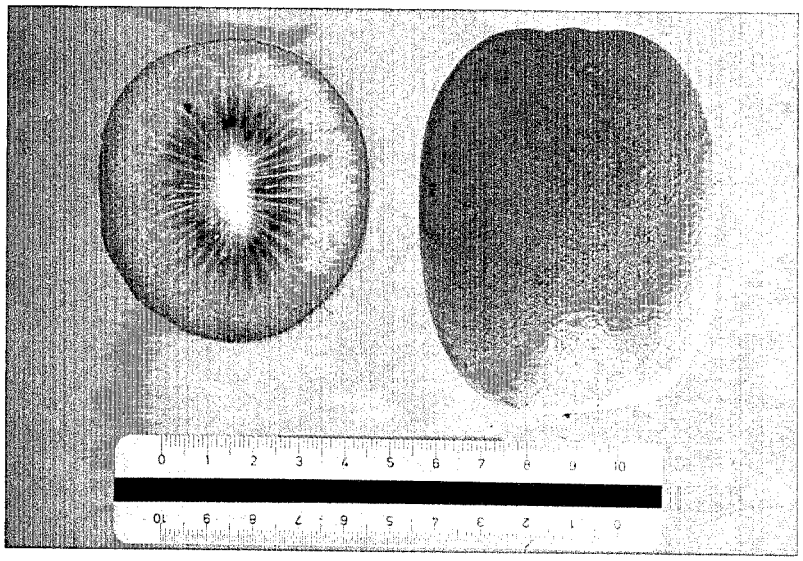
FIG. 5 shows a lateral view of the fruit and a transverse section.

FIG. 5 shows a lateral view of the fruit and a transverse section.

Figure 6:
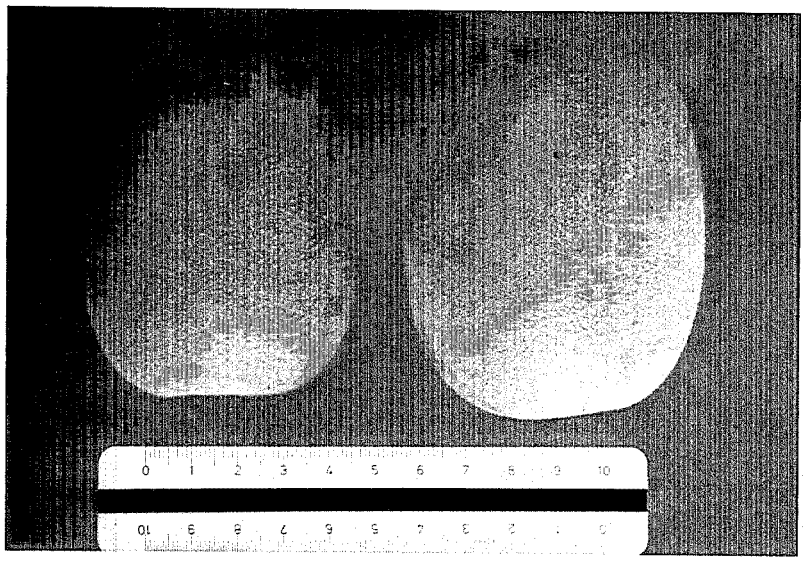
FIG. 6 shows two different lateral view of the fruit.

FIG. 6 shows two different lateral view of the fruit. The fruit skin has a silky aspect and there is an absence of long hairs typical of other kiwi varieties. The color of the skin is brownish-red, from near 176D to B to 177C, D, approaching near 174C to 175D but with reddish hues such as may be found in near 178B, although lighter. Fruit growing under shadow of branches and leaves may show somewhat different coloration from fruit growing in full sun. The remaining illustrations illustrate specimen fruit of the new variety in both transverse and longitudinal sections.

The following further horticultural observations were made of specimens grown in Verzuolo (Cuneo) Italy during the month of September.

PLANT

1. Plant:
   a) *Plant sex expression*—Female.
   b) *Vigor.*—Medium.
2. Young shoot:
   a) *Anthocyanin coloration of hairs.*—Medium.
   b) *Density of hair.*—Medium.
   c) *Length of hairs.*—Short.
   d) *Anthocyanin coloration in leaf axil.*—Weak.
3. Stem:
   a) *Color.*—Dark brown.
   b) *"Russet" on bark.*—Longitudinal.
   c) *Number of lenticels.*—Medium.
   d) *Conspicuousness of lenticels.*—Weak.
   e) *Size of wood bud support.*—Medium.
   f) *Leaf scar.*—Medium.
4. Young leaf:
   a) *General shape of blade.*—Cordate.
   b) *Shape of tip of blade.*—Acuminate.
   c) *Angel of apical part of blade.*—Acute.
   d) *Shape at base of blade.*—Overlapping.
   e) *Glossiness of upper surface of blade.*—Medium.
   f) *Density of hair on main veins on upper side of blade.*—Medium.
   g) *Density of absent or hair between main veins very sparse on upper side of blade.*—Sparse.
   h) *Density of hair on main veins on lower side of blade.*—Dense.
   i) *Density of hair between main veins on lower side of blade.*—Medium.
   j) *Anthocyanin coloration of petiole.*—Weak.
5. Mature leaf:
   a) *Color of upper side of blade.*—Light green.
   b) *Blistering of upper side of blade.*—Weak.
   c) *Spiny ciliation on margin of blade.*—Present.
   d) *Glossiness of upper surface of blade.*—Medium.
6. Inflorescence:
   a) *Predominant number of flowers.*—One.
7. Pedicel:
   a) *Length.*—Medium.
   b) *Length of hairs.*—Short.
8. Branch length:
   a) *Length of preexisting branches (determined in* 1992).—Average 168 cm, minimum 45 cm, maximum 338 cm.
   b) *Length of new branches (one year growth).*—Average 128 cm, minimum 45 cm, maximum 210 cm.
9. Internode length:
   a) *Base to first internode.*—Average 4.3 cm, minimum 1.0 cm, maximum 10.0.
   b) *First to second internode.*—Average 5.6 cm, minimum 2.0 cm, maximum 12.5.
   c) *Second to third internode.*—Average 7.7 cm, minimum 2.0 cm, maximum 12.0.
   d) *Third to fourth internode.*—Average 6.2 cm, minimum 0.5 cm, maximum 10.5.
   e) *Fourth to fifth internode.*—Average 6.7 cm, minimum 0.5 cm, maximum 12.0.
   f) *Average length, measured on 300 internodes.*—5.9 cm.
10. Leaf size (average of 100 samples):

a) *Width.*—Average 18.50 cm, minimum 15.20 cm, maximum 22.30 cm.

b) *Length.*—Average 16.20 cm, minimum 13.70 cm, maximum 19.10 cm.

c) *Area.*—Average 299.70 $cm^2$, minimum 208.40 $cm^2$, maximum 425.93 $cm^2$.

FLOWER

1. Flower:
   a) *Length of sepal.*—Short.
   b) *Color of sepal.*—White.
   c) *Length of petal.*—Medium.
   d) *Length/width ratio of petal.*—Less than twice as long as broad.
   e) *Position of petals.*—Overlapping.
   f) *Surface of petal.*—Smooth.
   g) *Curvature of petal.*—Cupped.
   h) *Petal shoulder.*—Present.
   i) *Number of styles.*—Few.
   j) *Attitude of styles.*—Semi-erect.
   k) *Tufts of hairs at base of styles.*—Present.
   l) *Number of stamens.*—Medium.

FRUIT

1. Fruit:
   a) *Size.*—Large.
   b) *Shape.*—Cylindrical.
   c) *Cross section.*—Circular.
   d) *Color of skin at harvest.*—Brownish-red, near 176 D to B.
   e) *Type of hair.*—Silky.
   f) *Density of hairs.*—Medium.
   g) *Length of hairs.*—Short.
   h) *Color of hairs at harvest.*—Light brown.
   i) *Stylar end.*—Hollow.
   j) *Diameter of columella in medium cross section*.—Medium.
   k) *Shape of columella in cross section.*—Elliptical.
   l) *Color of flesh.*—Light green.
2. Time of beginning of flowering: Early.
3. Time for maturity for harvest: Medium.
4. Time of leaf fall: Medium.

Note: the time of leaf fall largely depends on the environmental conditions. During a comparison test with the variety 'Hayward' carried out in a controlled planting located in Zona Verzuolo (Cuneo), meaningful differences have not been determined either in the time leaf fall starts or ends.

5. Botanical characteristics of the fruit a) Time of harvesting and characteristic of the fruit at the harvesting The following indicated characteristics are observed from plants growing in Zona Verzuolo (Cuneo), Northern Italy. The tests were carried out with a bench penetrometer, having a measure scale from 0 to 12 $kg/cm^2$ with a rounded-off probe having a diameter of 11 mm.

The sugar content of the flesh of the fruit has been determined in degree Brix (Bx°). A degree Brix represents the sugar content in 100 $cm^3$ if the solute is only sugar.

1991

Harvesting on October 16. Average Bx° 10.13, minimum 7.0, maximum 11.6.

Hardness (firmness) measured with 11 mm diameter probe: average 5.82 $kg/cm^2$, minimum 4.5, maximum 7.2.

1992

Harvesting on October 17. Average BX° 9.81, minimum 9.3, maximum 11.3.

Hardness (firmness) measured with 11 mm diameter probe: average 6.16 $kg/cm^2$, minimum 3.0. maximum 7.5.

b) Size of the fruit

The size of the fruit has been measured and averaged from 100 samples during the harvesting season 1992.

The data described below refers to the weight, to the length and so-called first width and second width of the fruit, which correspond respectively to the minor diameter of an ellipse and to the major diameter of an ellipse.

These two measures take into account the fact that fruit often does not show a perfectly cylindrical shape and therefore it is usual to take both diameters of the fruit so that a more meaningful indication of the fruit is obtained.

| | |
|---|---|
| (1) Weight | average 136.03 g, minimum 115.42 g, maximum 159.73 g (mean square deviation = 6.22) |
| (2) First width (minor diameter) | average 54.81 cm, minimum 51.10 cm, maximum 59.90 cm (mean square deviation = 0.99) |
| (3) Second width (major diameter) | average 58.06 cm, minimum 53.40 cm, maximum 63.40 cm (mean square deviation = 1.01) |
| (4) Length | average 66.95 cm, minimum 62.95 cm, maximum 70.95 (mean square deviation = 1.09) |

c) Color of the skin determined as an average of 100 samples of fruit

This test was performed using a Minolta chromameter CR-100 and using the Munsell Color Chart notation, that is, L (lightness or value), hue (a) and saturation (b).

| | |
|---|---|
| (1) Value L | average 53.93, minimum 49.28, maximum 53.93 |
| (2) Hue (a) | average +4.16, minimum +0.74, maximum +8.09 |
| (3) Saturation (b) | average +26.24, minimum +24.20, maximum +28.88 |

(4) Additionally, a determination according to the C.U.C. (Code Universal de Couleurs) E.SF.GUY (Le Chevalier Edition, Paris) has been carried out with the following results: C.U.C. 340 for the hair, C.U.C. between 261 and 337 for the skin.

d) Color of the flesh determined as an average of 100 samples of fruit

This determination has been carried out with the same instrument as used to determine skin coloration and uses the same Munsell notation.

| | |
|---|---|
| (1) Value L | average 47.59, minimum 38.46, maximum 54.42 |
| (2) Hue (a) | average −6.02, minimum −7.98, maximum −3.17 |
| (3) Saturation (b) | average +16.14, minimum |

-continued

| | |
|---|---|
| | +9.54, maximum +20.42 |

e) Size of the columella

The size of the columella determined as an average of 100 samples of fruit.

| | |
|---|---|
| (1) Width | average 0.8 cm, minimum 0.7 cm, maximum 1.2 cm |
| (2) Length | average 1.5 cm, minimum 1.2 cm, maximum 1.9 cm |

f) Number of seeds in comparison with the weight of the fruits

| | |
|---|---|
| (1) Weight 120–140 g | average 490, minimum 385, maximum 531 |
| (2) Weight 141–160 g | average 521, minimum 458, maximum 569 |
| (3) Weight 161–180 g | average 706, minimum 584, maximum 872 |
| (4) Weight 181–200 g | average 777, minimum 611, maximum 943 |

g) Acidity value of the fruit

The acidity value of the fruit has been obtained by neutralizing the total free acids with a 0.1N solution of NaOH and expressing the results as grams of acid per liter of solution:

(1) In malic acid 11.18 g/liter; in citric acid 10.68 g/liter; in tartaric acid 12.52 g/liter h) Size of the lenticels as an average of 100 samples of fruit

| | |
|---|---|
| (1) Length | average 2.06 mm, minimum 1.0 mm, maximum 3.2 mm |
| (2) Width | average 0.7 mm, minimum 0.5 mm, maximum 0.9 mm |

i) Taste

In comparison to the taste of the variety 'Hayward', the taste of 'K1 89' is less acid with particularly marked and intense aromas such as those of strawberry and raspberry.

j) Fibers of the flesh

The number of fibers in the flesh of the variety 'K1 89' is lower than in the case of the variety 'Hayward'. The flesh is substantially more compact and deliquescent at complete ripening.

k) Color of the seeds

The color of the seeds of the variety 'K1 89' is similar to the color of the seeds of the variety 'Hayward'.

l) Shipping and handling qualities of the variety

These qualities depend on the ripening of the fruits which, particularly in the case of the new variety, have to be picked well before the physiological ripening. In comparison to the variety 'Hayward', the new variety has a lower shipping and handling quality.

m) Storage quality

The storage life of the fruit is lower than in the case of the variety 'Hayward' and according to the available data is about 60–100 days in a controlled atmosphere.

n) Productivity of the variety 'K1 89'

The presently available date relates to the productivity of plants not completely mature. The determination carried out on these plants shows that the productivity of the variety 'K1 89' is high owing to the high percentage of shooting and the high fertility of the shoots. This suggests the desirability of a thinning of the plant to be carried out soon after the seed setting.

According to presently available information, the productivity of a plant of the variety 'K1 89' can be regarded as 60–70 kg/plant considering fruit of more than 90 g of weight and after the thinning of the plant. This high productivity should be considered not only in view of the number of fruit but also in respect to the high specific weight of the fruit.

I claim:

1. A new and distinct variety of kiwi plant of the species *Actinidia chinensis* P1. substantially as shown and described.

* * * * *